(12) United States Patent
Hodorek et al.

(10) Patent No.: US 11,129,719 B2
(45) Date of Patent: Sep. 28, 2021

(54) TRIAL RADIAL HEAD IMPLANT

(71) Applicant: Synthes GmbH, Oberdorf (CH)

(72) Inventors: Brian C. Hodorek, Winona Lake, IN (US); Matt J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 16/025,964

(22) Filed: Jul. 2, 2018

(65) Prior Publication Data

US 2019/0269516 A1    Sep. 5, 2019

Related U.S. Application Data

(60) Provisional application No. 62/638,844, filed on Mar. 5, 2018.

(51) Int. Cl.
*A61F 2/38* (2006.01)
*A61F 2/30* (2006.01)
*A61F 2/46* (2006.01)

(52) U.S. Cl.
CPC .......... *A61F 2/3804* (2013.01); *A61F 2/4684* (2013.01); *A61F 2002/30112* (2013.01); *A61F 2002/30934* (2013.01); *A61F 2002/3818* (2013.01); *A61F 2002/3827* (2013.01)

(58) Field of Classification Search
CPC .... A61F 2220/0025; A61F 2002/30604; A61F 2002/448; A61F 2/38; A61F 2/3804; A61F 2002/30331; A61F 2002/30341; A61F 2002/30367; A61F 2002/30405; A61F 2002/3809; A61F 2002/3813; A61F 2002/3818; A61F 2002/3827; A61F 2002/4435
See application file for complete search history.

(56) References Cited

U.S. PATENT DOCUMENTS

| | | | |
|---|---|---|---|
| 6,746,487 B2 | 6/2004 | Scifert et al. | |
| 7,740,661 B2 | 6/2010 | Baratz et al. | |
| 8,535,382 B2 | 9/2013 | Kehres et al. | |
| 8,764,845 B2 | 7/2014 | Brooks et al. | |
| 8,840,676 B2 | 9/2014 | Belew et al. | |
| 8,945,138 B2 | 2/2015 | Klotz et al. | |
| 9,707,084 B2 * | 7/2017 | Huebner | A61F 2/3804 |
| 9,746,487 B2 | 8/2017 | Marty et al. | |
| 2004/0186580 A1 | 9/2004 | Steinmann | |
| 2005/0075735 A1 | 4/2005 | Berelsman et al. | |
| 2005/0216090 A1 * | 9/2005 | O'Driscoll | A61F 2/3804 623/20.32 |
| 2012/0083892 A1 * | 4/2012 | Kehres | A61F 2/3804 623/20.11 |
| 2016/0051365 A1 | 2/2016 | Brownhill et al. | |

* cited by examiner

*Primary Examiner* — Ann Schillinger
(74) *Attorney, Agent, or Firm* — BakerHostetler

(57) ABSTRACT

A trial orthopedic implant having a plurality of bearing component augments of differing heights, where each augment releasably, slidably connected to the trial implant.

5 Claims, 8 Drawing Sheets

TRIAL RADIAL HEAD IMPLANT

BACKGROUND

1. Field of the Invention

The present invention relates generally to trial orthopedic implant devices and systems and, more particularly to trial orthopedic implant devices and systems for determining the height of a final radial head implant.

2. Description of the Related Art

Some fractures of the radius occur in the part of the bone that is proximate the elbow, called the radial "head". Radial head fractures are common injuries that may result from an acute elbow injury. Fractures of the radial head are typically treated with a variety of surgical and non-surgical options depending upon the severity of the injury. For example, surgical options for more severe injuries to the radial head can include open reduction with internal fixation (ORIF), radial head resection, hemi-arthroplasty (e.g., radial head arthroplasty), and total arthroplasty (i.e., total elbow replacement).

Radial head arthroplasty involves resecting the fractured and damaged radial head and replacing the natural articulation with an artificial one by use of an implant. The implant articulates with the natural cartilage surface of the capitellum of the distal humerus.

In radial head replacement procedures, a radial head prosthesis is implanted into the intramedullary canal of the proximal radius. The radial head may cooperate with an ulna or ulnar prosthesis to provide radioulnar joint articulation. The radial head may cooperate with a humerus or humeral prosthesis to provide radiohumeral joint articulation.

Prior to implantation of a radial head implant, a surgeon will need to select an implant having a size that properly fits the implant site of the particular patient. Many known systems include trial stems and trial heads the surgeon can assemble and use prior to final implantation to evaluate the fit for selecting the most appropriately sized implant. However, known systems do not offer a simple effective means for trying a plurality of different humeral head heights to determine the proper height for a final radial head implant. Exemplary systems include the following prior art devices:

U.S. Pat. No. 6,746,487 discloses an intramedullary fixation device for use in securing a trial in the medullary canal of a bone to determine the offset and orientation of a prosthetic implant for replacement of a joint articulating surface of the bone is disclosed. The fixation device comprises a body for receiving a trial and a fixation portion for engaging the trial. A system for use in surgical repair of a joint comprising a selection of prosthetic implants of various sizes, a selection of trials of various sizes corresponding to the sizes of the implants, a selection of fixation devices of various sizes corresponding to the sizes of the trials, a trial fixation device driver for inserting the fixation device and attached trial into the canal of a bone, and a trial device extractor for removing the fixation device from the resected bone is disclosed. Methods of using the fixation device and system of the invention are disclosed.

U.S. Pat. No. 7,740,661 discloses radial head implant apparatuses and methods. In one embodiment, a radial head implant can include a head portion for articular engagement with a humerus bone, a stem portion for engagement with a radius bone, and a shaft for engagement with the stem portion. The head portion can include an upper surface for engaging the humerus bone. The stem portion can have an axial opening for receiving at least a portion of the shaft, and a collar can be disposed around the stem portion at a proximal end thereof. An upper portion of the shaft can be configured for engaging the head portion, while a lower portion of the shaft can be elongated and cylindrical for axially fitting into and moving within the axial opening of the stem portion. Other embodiments are also disclosed for axial movement for a radial head implant. Various structures are disclosed for locking the shaft in position within the stem portion.

U.S. Pat. No. 8,535,382 discloses a prosthesis system for replacement of a head portion of a proximal radius. The system can include a first polymeric articulation component having a first locking portion and a metal head component having a second locking portion. The second locking portion can mate with the first locking portion to form a first locking mechanism to initially couple the first articulation component to the head component. The head component can define a locking channel. The system can also include a stem component having a protrusion receivable in the locking channel. The protrusion can define a bore, and the stem component can be adapted to be coupled to the radius. The system can also include a fastener received through the locking channel and into the bore to provide a second locking mechanism that couples the head component to the stem component.

U.S. Pat. No. 8,764,845 discloses a kit for use in a procedure for implantation of an orthopaedic joint prosthesis includes a head component of an orthopaedic joint prosthesis, which comprises a body part having a convex bearing surface, and a reverse face at which the head component can be connected to a mating component of the joint prosthesis, in which the head component has a chamfer surface extending around at least part of its periphery where the bearing and reverse faces come together, and a plurality of markings on the chamfer surface. The kit includes a trial head component which comprises a body part having a convex trial bearing surface and a reverse face, in which the trial head component has a plurality of markings on the trial bearing surface at or towards the interface between it and the reverse face. The transverse dimensions of the head component are approximately the same as the transverse dimensions of the trial head component, and in which the location of the markings on the chamfer surface around the periphery of the head component corresponds to the location of the markings on the trial bearing surface of the trial head component around its periphery.

U.S. Pat. No. 8,840,676 discloses a prosthesis trial system includes at least one head member having an outer surface and a cavity configured to mate with an exterior surface of a stem member. The prosthesis trial system further includes at least one shell member having an inner surface configured to mate with the outer surface of the at least one head member.

U.S. Pat. No. 8,945,138 discloses a kit for use in performing a trial reduction in joint arthroplasty is provided. The kit includes a trial stem assembly including a first component, a second component selectably moveable with respect to the first component, and a fastener for securing the first component to the second component. The kit also includes an articulating trial component removeably fixedly secured to the trail stem assembly and a driver for cooperation with the fastener to secure the first component to the second component. The kit also includes a handle. The handle has a first feature for permitting the driver to pass through the handle and a second feature for orientably connecting the handle to the articulating trial component.

U.S. patent application publication no. 20040186580 discloses a radial head replacement system includes a radial head replacement, an apparatus for guiding the resection of a radial head, and a kit including bone plug and bone plug insertion instrument. The radial head replacement has a separate adjustable head portion that may be secured on an implanted stem such that the implanted radial head replacement smoothly interfaces with the capitellum of the humerus. In another form, the radial head replacement uses crossed bone screws that serve to more securely anchor the stem of the radial head replacement in the intramedullary canal of the radius. The resection guide includes a movable cutting guide which ensures a precise resection of the radial head and thereby allows for better positioning of the implanted radial head replacement. The bone plug limits the travel of bone cement beyond the area of affixation of the stem portion of a radial head replacement to the radius.

U.S. patent application publication no. 20050075735 discloses a modular prosthesis system for replacement of a head portion of a radius. The prosthesis system includes a head component having a first connection portion that connects to a second connection portion and a collar component having the second connection portion and a third connection portion. The system also includes a stem component including a fourth connection portion that connects with the third connection portion, the stem component having a stem anchoring portion that connects to the radius. The collar component provides the modular geometry to the prosthesis without having to have an increased number of head components and stem components with variable lengths and angles.

U.S. patent application publication no. 20160051365 discloses a radial head trial device for replacement of a proximal radial head includes a stem component having a center longitudinal axis extending between a proximal end and a distal end, a head component axially and removably attachable to the stem component, wherein the head component is interchangeable with a selection of other head components each axially and removably attachable to the stem component, an anti-rotation feature, and a recess, wherein the anti-rotation feature is structured to be received in the recess to prohibit rotation of the head component relative to the stem component.

What is needed in the art is a trial radial head implant device and system that allows less joint distraction and a simpler device for confirming final implant height.

SUMMARY

In one exemplary embodiment, the present invention is presented as a trial orthopedic implant assembly apparatus, said implant assembly apparatus comprising: a radial implant component, said radial implant component having a generally cylindrical head, said head having a height, a concave articular proximal surface, an opposing flat distal surface, a side wall, and a slot, said slot disposed through said wall of said head; said radial implant component further comprising a stem, said stem extending from said distal surface of said head; a head augment, said augment having a generally cylindrical shape, a concave articular proximal surface, an opposing distal concave mating surface, and a side wall, said augment having a height, where said height of said augment is less than the height of said head; said head augment further comprising a base, said base comprising an extension member, said extension member having a first end connected to said mating surface of said augment and extending vertically away from said mating surface of said augment such that said extension member is perpendicular to said mating surface of said augment, said extension member further comprising a second end opposite said first end; and a tab, said tab extending from said second end of said extension member, said tab perpendicular to said extension member, said tab releasably slidably inserted and connected into said slot of said head component such that said mating surface is disposed against said proximal articular surface of said head component.

In another exemplary embodiment, the present invention is presented as a trial orthopedic implant system, said implant system comprising: a radial implant component, said radial implant component having a generally cylindrical head, said head having a height, a concave articular proximal surface, an opposing flat distal surface, a side wall, and a slot, said slot disposed through said wall of said head; a stem, said stem extending from said distal surface of said head; a plurality of head augments, each head augment of said plurality of augments having a generally cylindrical shape, a concave articular proximal surface, an opposing distal concave mating surface, and a side wall, and a unique height, where said height of each said augment of said plurality of augments is less than the height of said head; each said augment further having a base, said base comprising an extension member, said extension member having a first end connected to said mating surface of said augment and extending vertically away from said mating surface of said augment such that said extension member is perpendicular to said mating surface of said augment, said extension member further comprising a second end opposite said first end; and a tab, said tab extending from said second end of said extension member, said tab perpendicular to said extension member, said tab releasably slidably inserted and connected into said slot of said head component such that said mating surface is disposed against said proximal articular surface of said head.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
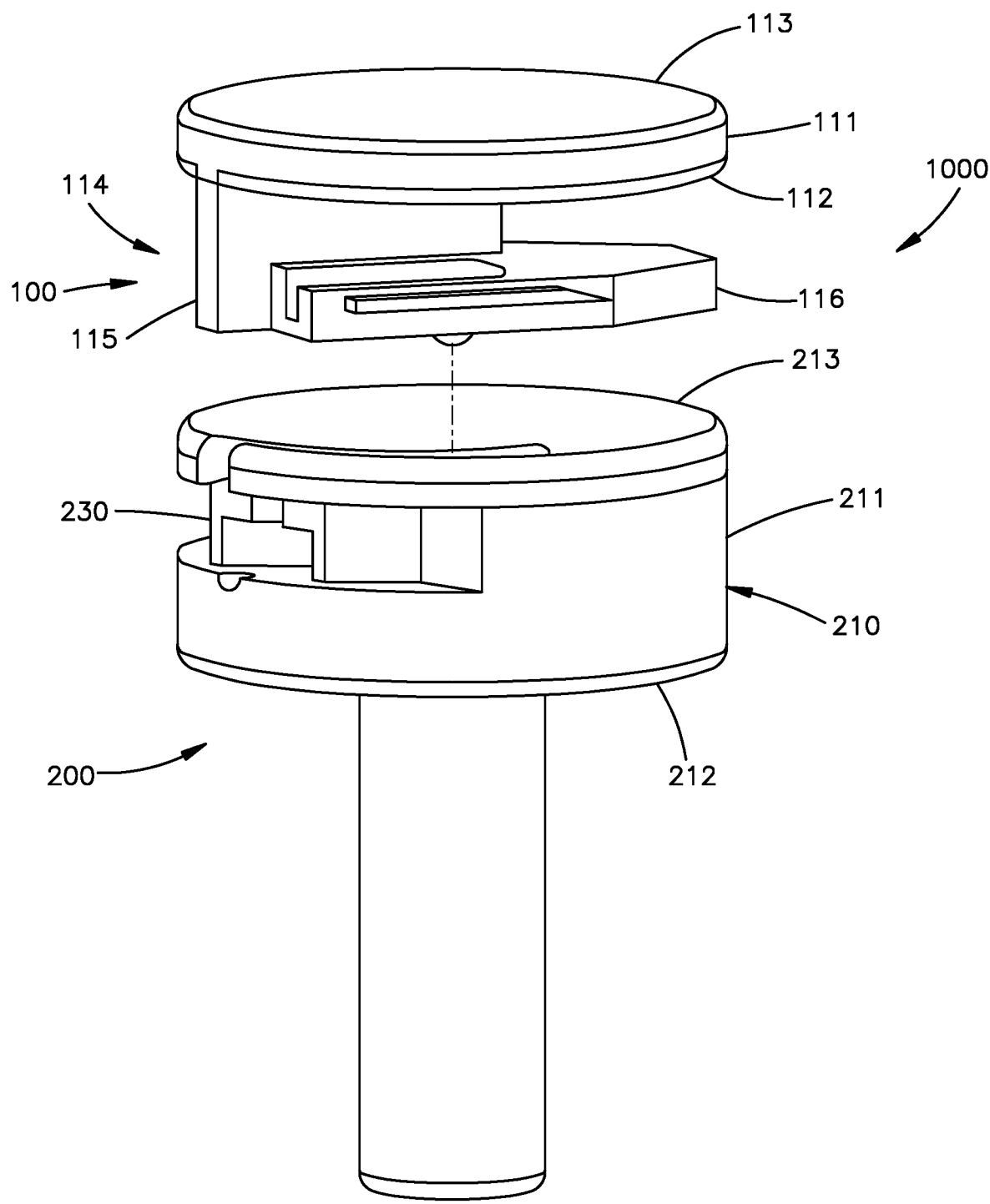
FIG. 1 shows a side perspective exploded view of a trial radial implant apparatus and radial head augment apparatus in accordance with an exemplary embodiment of the present invention.
Figure 2:
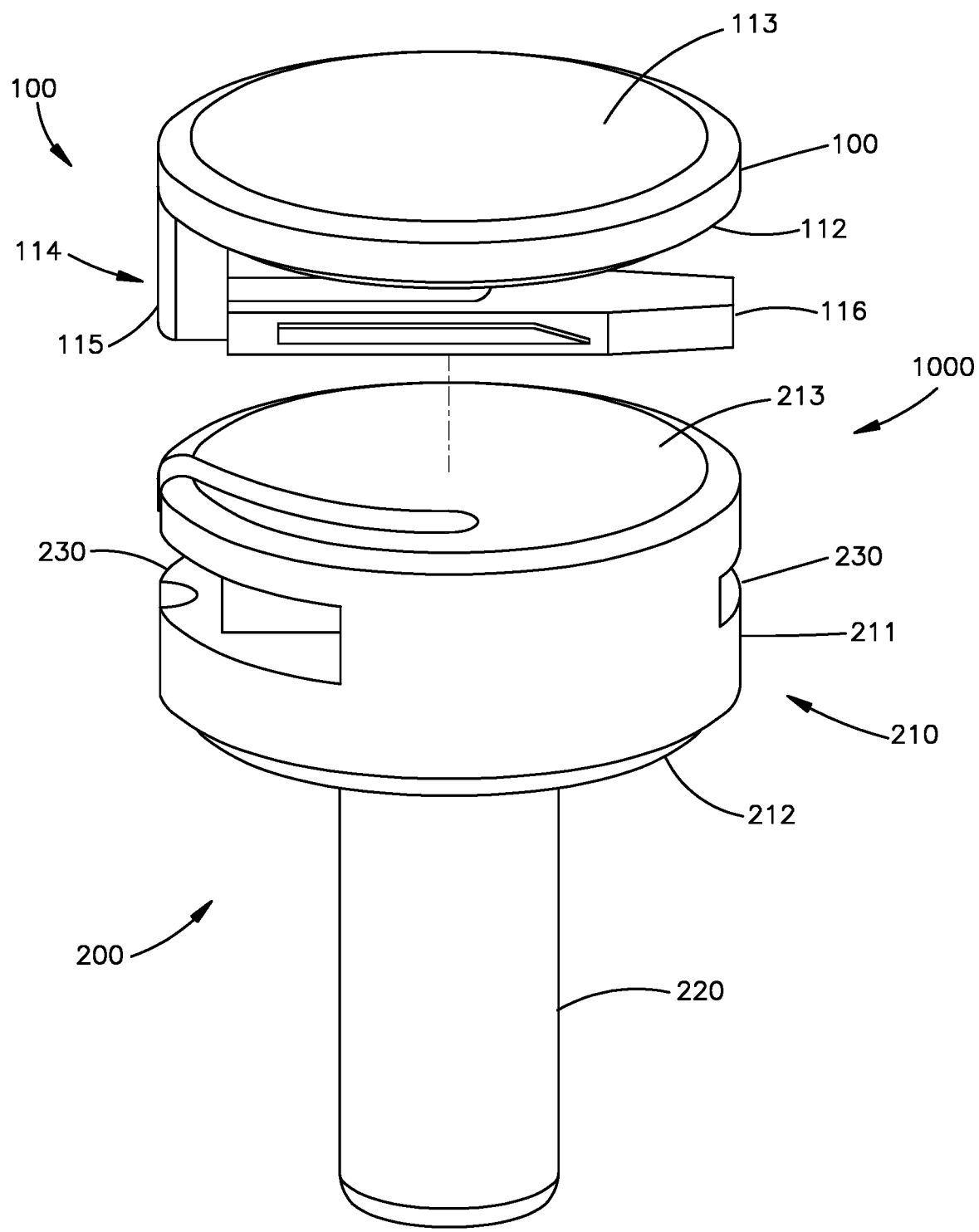
FIG. 2 shows another side perspective exploded view of a trial radial implant apparatus and radial head augment apparatus in accordance with an exemplary embodiment of the present invention.
Figure 3:
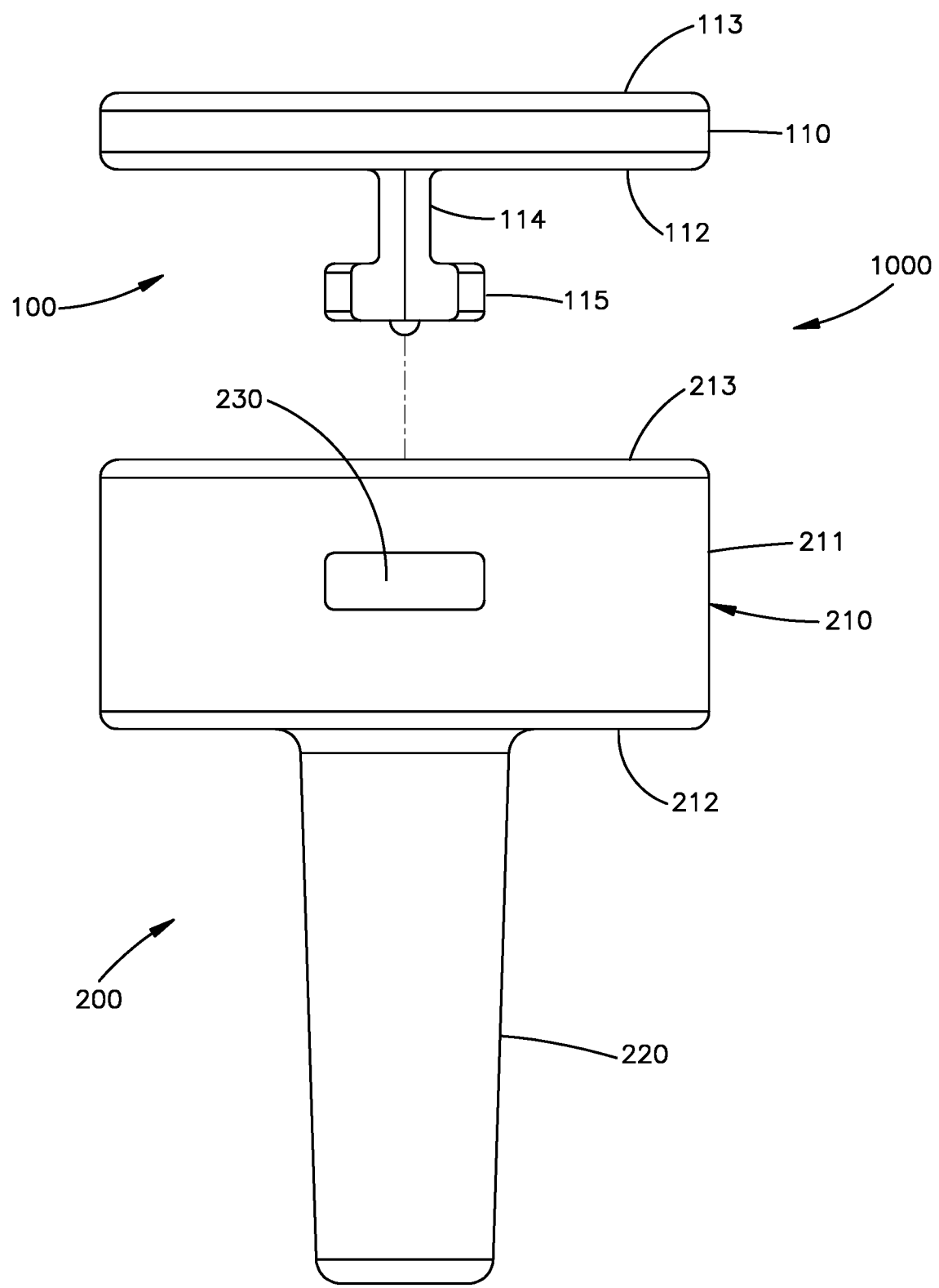
FIG. 3 shows a rear exploded view of a trial radial implant apparatus and radial head augment apparatus in accordance with an exemplary embodiment of the present invention.
Figure 4:
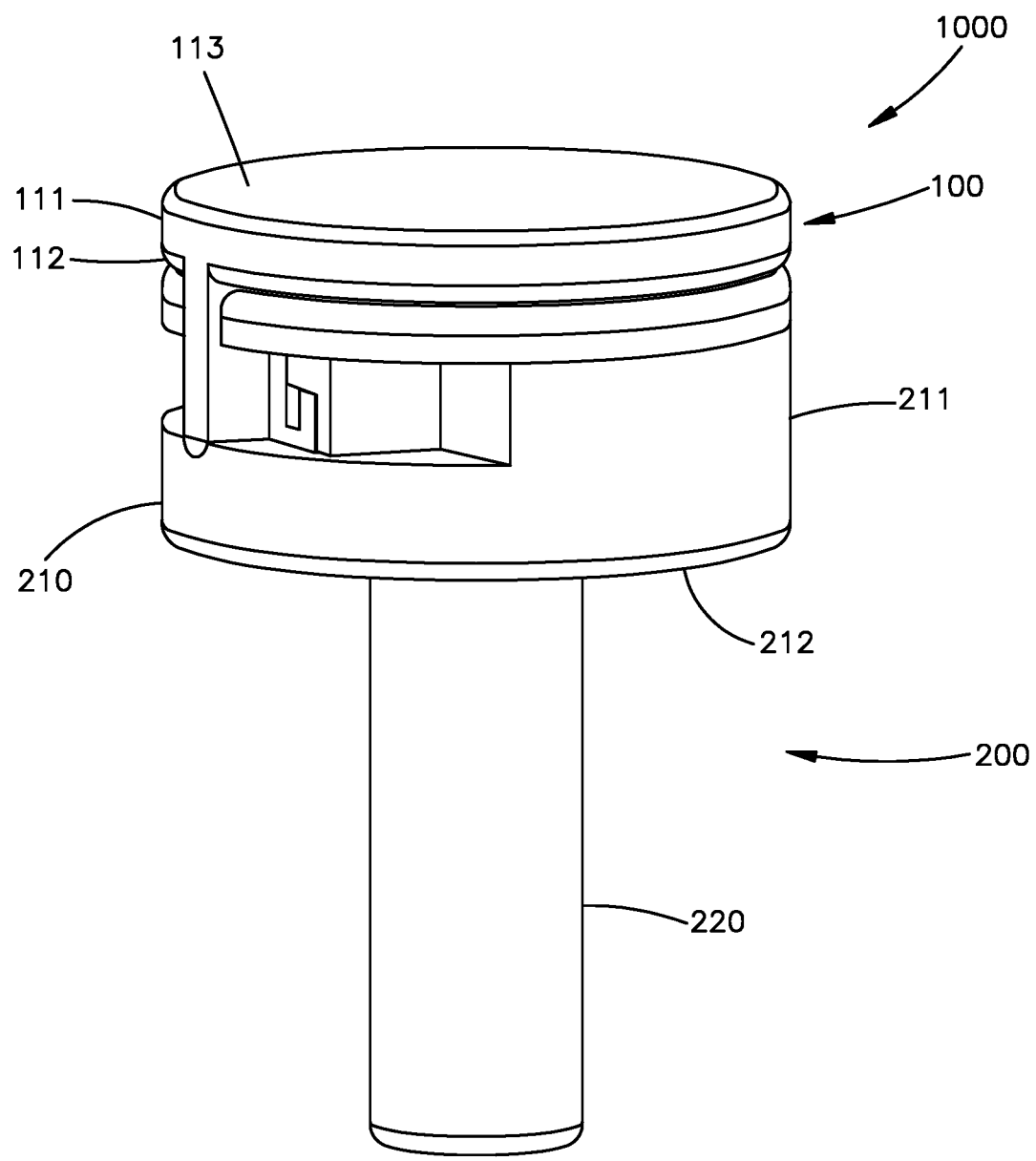
FIG. 4 shows a perspective view of a trial radial implant apparatus and radial head augment apparatus in accordance with an exemplary embodiment of the present invention.

Referring now collectively to FIGS. 1-3, where there are shown a perspective exploded views of a trial radial implant apparatus 1000 and to FIG. 4, which shows a perspective assembly view of 1000, apparatus 1000 generally comprises radial head augment 100 and radial head implant 200. Augment 100 is adapted to be releasably attached to radial head implant 200.

Figure 8:
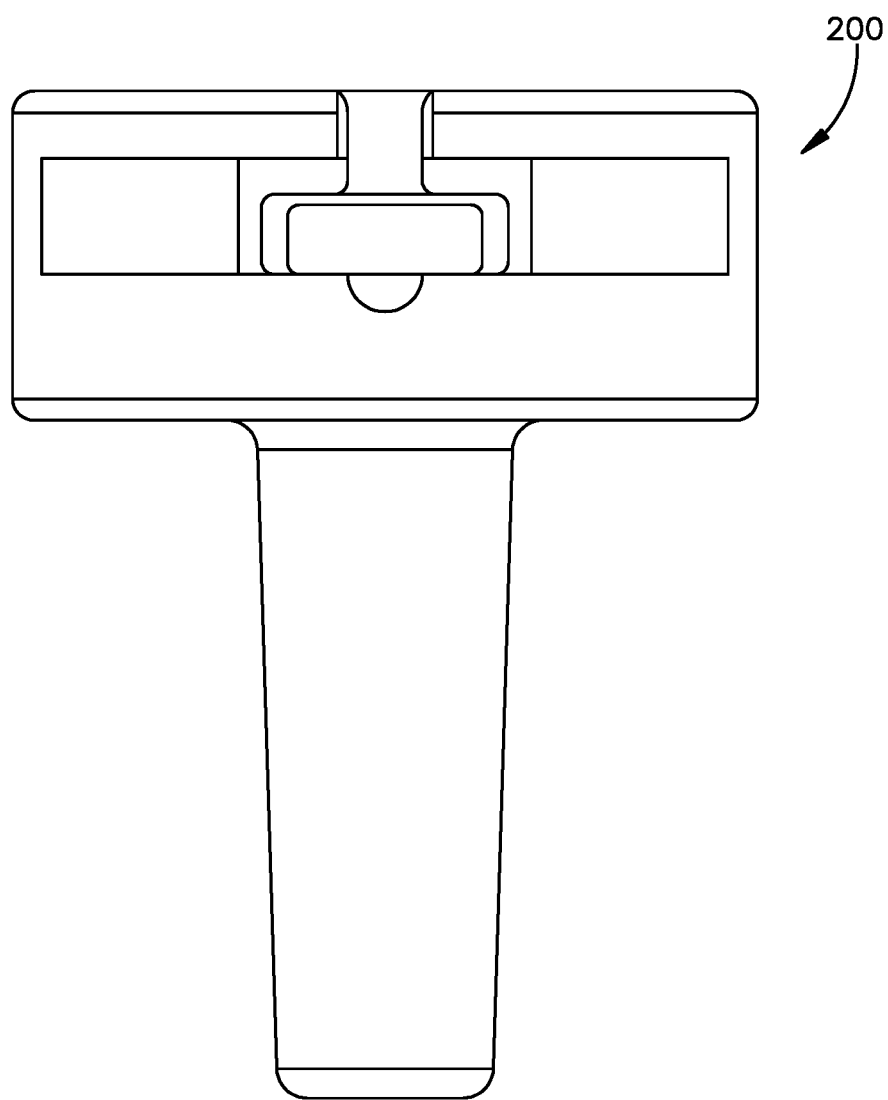
FIG. 8 shows a trial radial head implant apparatus in accordance with an exemplary embodiment of the present invention.

Referring now collectively to FIGS. 1-3, where there are shown a perspective exploded views of a trial radial implant apparatus 1000 and to FIG. 8, which shows a side view of implant 200, radial head implant 200 comprises head 210. Head 210 has a cylindrical shape with a flat side walls 211, a generally flat distal surface 212, and a concave, proximal, articular surface 213 disposed opposite distal surface 212. Head 210 further comprises a height. Radial implant 200 further comprises stem 220. As shown in FIGS. 1-3 and 8, stem 220 is connected (preferably fixedly) to and extends from surface 212 of head 210.

Referring still to FIGS. 1-3 and 8, radial implant 200 of assembly 1000 further comprises slot 230 disposed through wall 211 of head 210. Slot 230 is adapted to releasably receive tab 115 of augment 100 as described in greater detail below.

Figure 7:
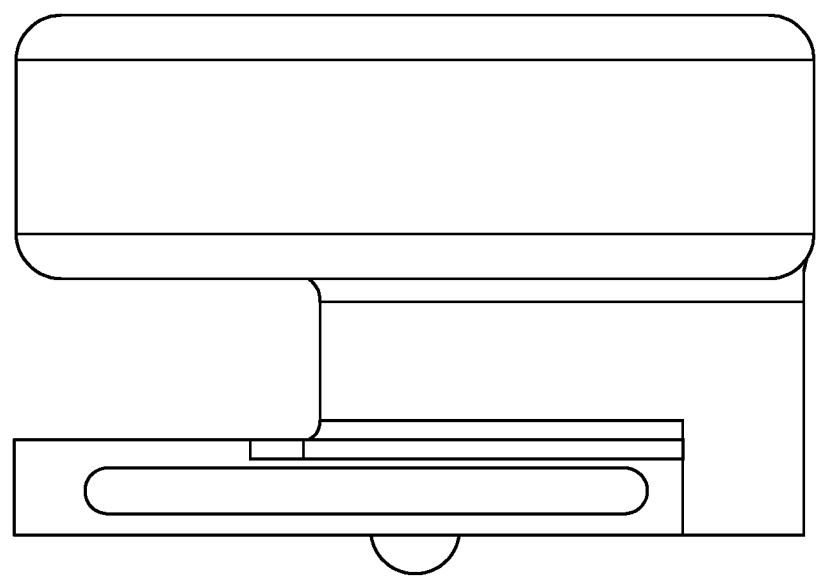
FIG. 7 shows a side view of a trial radial head augment for a trial radial implant apparatus in accordance with an exemplary embodiment of the present invention.

Referring now collectively to FIGS. 1-3, where there are shown a perspective exploded views of a trial radial implant apparatus 1000 and to FIG. 7, which shows a side view of augment 100, head augment 100 has a generally cylindrical shape with a proximal (upper) concave articular surface 113. Augment 100 further comprises a height. The height of augment 100 is less than the height of head 210. Augment 100 further comprises distal mating surface 112 disposed opposite proximal, articular surface 113. Mating surface 112 is preferably convex and adapted to nest against proximal articular surface 213 of head 210 of radial implant 200.

Referring again to FIGS. 1-3 and 7, augment 100 further comprises a base 114 having extension member 115. Extension member 115 is connected to and protrudes from distal, mating surface 112 of augment 100. Base 114 further comprises a tab 116 extending from perpendicularly from extension member 115. Tab 116 is generally parallel to mating surface 112 of augment 100.

Figure 5:
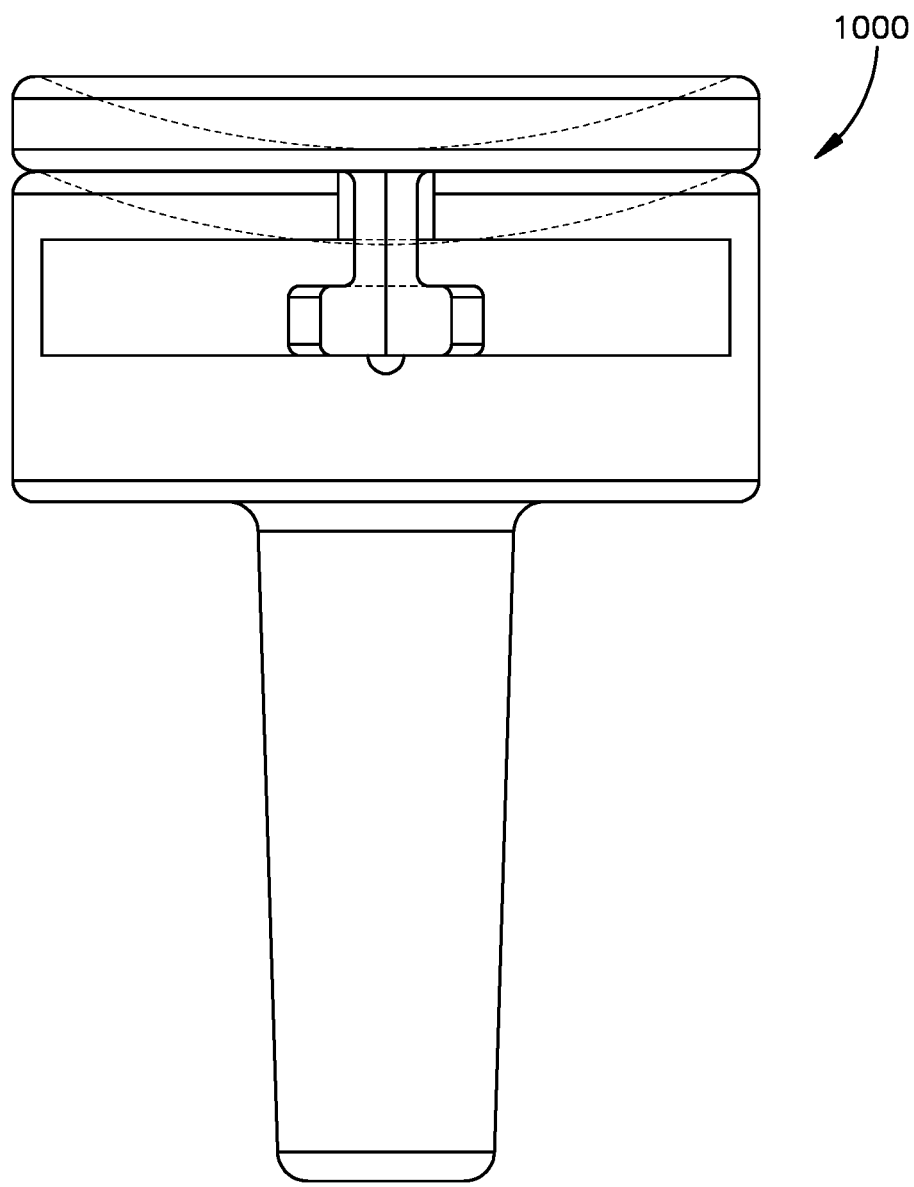
FIG. 5 shows a side cross-sectional view of a trial radial implant apparatus and radial head augment apparatus in accordance with an exemplary embodiment of the present invention.
Figure 6:
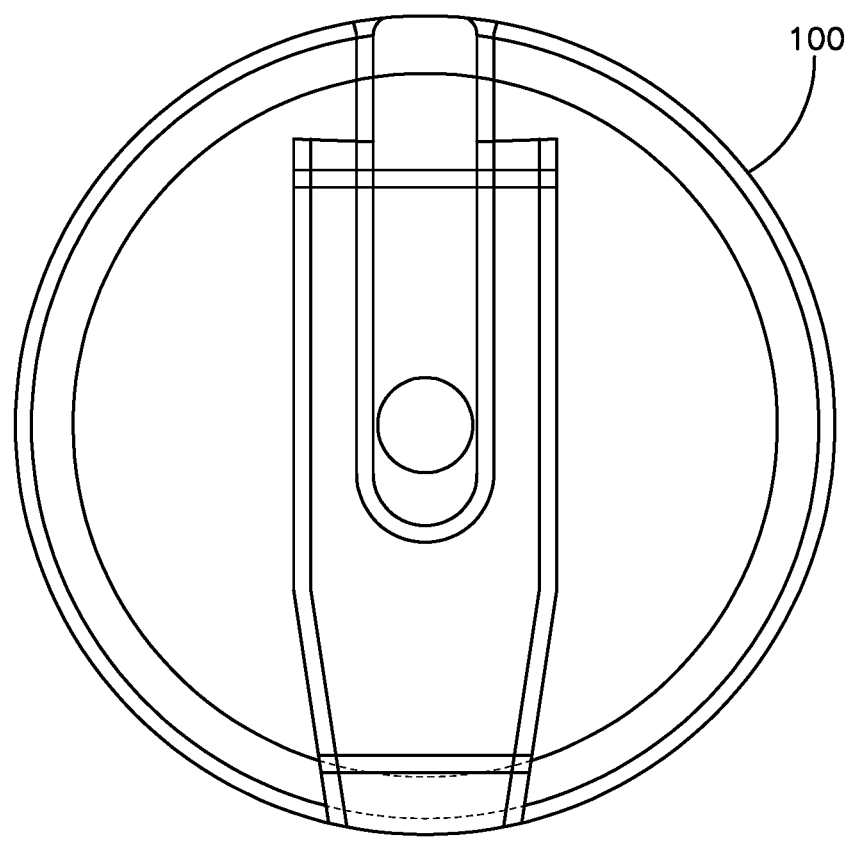
FIG. 6 shows a top cross-sectional view of a trial radial implant apparatus and radial head augment apparatus in accordance with an exemplary embodiment of the present invention.

Referring next to FIG. 4-6, there are shown perspective, side cross-sectional, and top assembly views respectively of assembly 1000 in accordance with an exemplary embodiment of the present invention. As illustrated in FIGS. 4-6, tab 116 is adapted to slidably, releasably engage with slot 230 of head 210. As further illustrated in FIGS. 4-6, mating surface 112 of augment 100 is adapted to abut concave articular surface 213 of head 210 when tab 116 of augment 100 is inserted into slot 230 of head 210.

It is a further aspect of the present invention that a system in accordance with the present invention may include a plurality of augments 100 wherein each augment 100 has a different unique height. A surgeon can then use assembly 1000 to determine the desired height for a non-trial implant by trying augments 100 until a preferred size is identified.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An orthopedic implant assembly comprising:
   a trial orthopedic implant assembly comprising:
      a radial implant component, said radial implant component having a generally cylindrical head, said head having a proximal surface and a distal surface opposite the proximal surface, the head of the radial implant component having a height from the proximal surface to the distal surface;
      said radial implant component further comprising a stem fixedly connected to said head, said stem extending vertically from said distal surface of said head; and
      a head augment having a generally cylindrical shape, a concave articular proximal surface, and an opposing distal mating surface, and a side wall, said head augment having a height, where said height of said head augment is less than the height of said head of said radial implant component; and said head augment further comprising a base that includes an extension member and a tab that extends from the extension member, said extension member having a first end that extends from said distal mating surface and extends vertically away from said distal mating surface;

wherein the tab is configured to connect to said head such that said distal mating surface is disposed against said head; and a final radial head implant having a height determined based on the height of the head augment; and wherein the proximal surface of the head is a concave articular proximal surface, the distal surface of the head is an opposing flat distal surface, and the head further defines a side wall from the concave articular proximal surface to the flat distal surface, and a slot that extends through the side wall of the head.

2. A trial orthopedic implant system, said implant system comprising the trial orthopedic implant assembly apparatus of claim 1, wherein the head augment comprises a plurality of head augments that each have a unique height less than the height of said head.

3. The orthopedic implant assembly of claim 1, wherein the distal mating surface of the head augment is convex.

4. The orthopedic implant assembly of claim 3, wherein the tab is releasably slidably insertable into the slot, such that the distal mating surface is disposed against the head.

5. The orthopedic implant assembly of claim 4, wherein the distal mating surface is disposed against the proximal surface of the head.

* * * * *